US005965175A

United States Patent [19]
Reinhart et al.

[11] Patent Number: 5,965,175
[45] Date of Patent: Oct. 12, 1999

[54] COMPOSITION AND METHOD FOR REPARTITIONING NITROGEN AND INCREASING COLONIC BLOOD FLOW IN DOGS TO PROMOTE INTESTINAL HEALTH

[75] Inventors: Gregory Allen Reinhart, Dayton; Gregory Dean Sunvold, Eaton, both of Ohio

[73] Assignee: The Iams Company, Dayton, Ohio

[*] Notice: This patent is subject to a terminal disclaimer.

[21] Appl. No.: 08/827,405

[22] Filed: Mar. 27, 1997

[51] Int. Cl.⁶ .................................................. A23K 1/00
[52] U.S. Cl. .............................. 426/2; 426/53; 426/54; 426/635; 426/658; 426/805
[58] Field of Search ................. 426/2, 635, 53, 426/54, 805, 658; 514/54, 867, 892

[56] References Cited

U.S. PATENT DOCUMENTS

| | | | |
|---|---|---|---|
| 4,044,158 | 8/1977 | Burkwall, Jr. | 426/27 |
| 5,017,389 | 5/1991 | Green | 426/72 |
| 5,312,638 | 5/1994 | Traitler et al. | 426/531 |
| 5,397,803 | 3/1995 | Smith et al. | 514/563 |
| 5,616,569 | 4/1997 | Reinhart | 514/54 |
| 5,684,045 | 11/1997 | Smith et al. | 514/563 |

FOREIGN PATENT DOCUMENTS

| | | |
|---|---|---|
| 0 674 842 A1 | 10/1995 | European Pat. Off. . |
| WO 9603150A1 | 2/1996 | WIPO . |

OTHER PUBLICATIONS

M.D. Howard et al, "Effect of fermentable fiber consumption by the dog on nitrogen balance and fecal microbial nitrogen extretion", FASEB J. 10:A257 (1996).

H. Younes et al, "Fermentable Fibers or Oligosaccharides Reduce Urinary Nitrogen Excretion by Increasing Urea Disposal in the Rat Cecum", Am. Inst. Nutrition, pp. 1010–1016, 1995.

Kerley et al, "Physiological Response to Short Chain Fatty Acid Production in the Intestine", *Proceedings of the 1996 Iams International Nutrition Symposium*, pp. 33–39, c. 1996.

G.D. Sunvold et al, "Dietary Fiber for Dogs: IV. In Vitro Fermentation of Selected Fiber Sources by Dog Fecal Inoculum and In Vivo Digestion and Metabolism of Fiber–Supplemented Diets", *J. Anim. Sci.* 1995, 73:1099–1109.

M.D. Howard et al, Effect of fermentable fiber consumption by the dog on nitrogen balance and fecal Microbial nitrogen excretion, FASEB Journal, vol. 10, 1996, p. A257, XP002072350.

G.D. Sunvold et al., "Dietary fiber for dogs: IV. In vitro fermentation of selected fiber sources . . . Supplemented diets", *Journal of Animal Science*, vol. 73, 1995, pp. 1099–1109, XP002072351.

M. Dietz et al., "Influence of a blend of fructo–oligosaccharides and sugar beet fiber on nutrient digestibility and plasma metabolite concentrations in healthy Beagles" *American Journal of Veterinary Research*, vol. 58, No. 11, 1997, pp. 1238–1242, XP–002072352.

Willard M D et al., Effects of Dietary Supplementation of Fructo–Olgosaccharides On Small Intestinal Bacterial Overgrowth in Dogs:, Amer. Journ. Of Veter. Research, vol. 55, May 1994, pp. 654–659.

*Primary Examiner*—Nina Bhat
*Attorney, Agent, or Firm*—Killworth, Gottman, Hagan & Schaeff, LLP

[57] ABSTRACT

A pet food product and process for repartitioning nitrogen and increasing colonic blood flow in dogs is provided which involves feeding a dog a diet of a pet food composition containing fermentable fibers which have an organic matter disappearance of 15 to 60 percent when fermented by fecal bacteria for a 24 hour period, the fibers being present in amounts from about 1 to 11 weight percent of supplemental total dietary fiber. The dog is maintained on the diet for a sufficient period of time to allow the fermentable fibers to ferment in the colon of the dog. The fermentation results in an increased quantity of bacteria in the colon of the dog, resulting in increased nitrogen excretion through the feces of the dog.

23 Claims, 2 Drawing Sheets

COMPOSITION AND METHOD FOR REPARTITIONING NITROGEN AND INCREASING COLONIC BLOOD FLOW IN DOGS TO PROMOTE INTESTINAL HEALTH

BACKGROUND OF THE INVENTION

This invention relates to a pet food product for use in repartitioning nitrogen and increasing colonic blood flow in dogs to promote intestinal health, and more particularly to a process involving a pet food composition containing fermentable fibers.

Many dogs suffer from poor health due to renal insufficiency. It is desirable to reduce the stress placed on the kidneys of dogs with this condition. One factor that contributes to such stress is nitrogen-containing metabolites in the blood.

Nitrogen in the blood is primarily removed by the kidneys. Weakened kidneys can be overworked attempting to remove nitrogen from the blood, resulting in renal failure. Therefore, a need exists for a method of reducing the amount of nitrogen in the blood of dogs without using the kidneys.

In extreme cases, medical devices such as dialysis machines can be used to remove nitrogen in the blood. However, in the case of dogs this approach is usually cost prohibitive. Also, most cases of renal insufficiency are less extreme, therefore, less invasive techniques are desirable. Particularly desirable are low cost techniques that are easy to administer.

Some research has been done in the area of nitrogen repartitioning. This involves using bodily methods of waste removal other than the kidneys to eliminate nitrogen from the blood. Younes et al., FASEB J. 8:A186 (1994) (Abstract) have experimented with using a fermentable fiber-containing diet to increase urea disposal in the rat cecum. However, those experiments were limited to the rat which has a different metabolism than the dog. For example, the dog has a nonsacculated intestine as opposed to the sacculated intestine in the rat; the dog has a nonfunctional cecum as opposed to a functional cecum in the rat; and the dog does not practice coprophagy as does the rat.

Therefore, a need still exists for a low cost, easy to administer method of reducing the amount of nitrogen in the blood of dogs without using the kidneys. There is also a need for a method for increasing blood flow to the colon of a dog to enhance and promote intestinal health.

SUMMARY OF THE INVENTION

This need is met by the present invention, wherein nitrogen is repartitioned in dogs by increasing nitrogen excretion via the colon. The process and product of the present invention also increases blood flow to the colon, increasing the amount of nitrogen excreted. This results in health benefits by reducing the strain on the kidneys of the dog. In addition, the increased colonic blood flow promotes a healthy gut by keeping the colonic tissues infused.

In one embodiment of the present invention, a process for repartitioning nitrogen in dogs is provided. The process involves feeding a dog a diet of a pet food composition containing fermentable fibers which have an organic matter disappearance of 15 to 60 percent when fermented by fecal bacteria for a 24 hour period, the fibers being present in amounts from about 1 to 11 weight percent of supplemental total dietary fiber. The dog is maintained on the diet for a sufficient period of time to allow the fermentable fibers to ferment in the colon of the dog. The fermentation results in an increased quantity of bacteria in the colon of the dog, resulting in nitrogen being excreted through the feces of the dog. The fermentation also provides enhanced metabolic fuel availability, in the form of short chain fatty acids such as, for example, butyrates which are utilized by canine intestinal cells. Finally, dogs fed a diet containing fermentable fibers exhibit increased colonic blood flow, with such increased blood flow providing additional metabolic fuel such as, for example, glucose, to canine intestinal cells.

Preferably, the pet food composition contains from 2 to 9 weight percent of supplemental total dietary fiber of fermentable fibers. More preferably, the pet food composition contains from 3 to 7 weight percent of supplemental total dietary fiber of fermentable fibers. Most preferably, the pet food composition contains from 4 to 7 weight percent of supplemental total dietary fiber of fermentable fibers.

Preferably, the fermentable fibers have an organic matter disappearance of 20 to 50 percent. More preferably, the fermentable fibers have an organic matter disappearance of 30 to 40 percent.

In addition, the fermentable fibers are preferably selected from the group consisting of beet pulp, gum arabic, gum talha (a form of gum arabic), psyllium, rice bran, carob bean gum, citrus pulp, pectin, fructooligosaccharides, mannanoligosaccharides and mixtures thereof. More preferably, the fermentable fibers are selected from the group consisting of beet pulp, gum arabic and fructooligosaccharides. Most preferably, the fermentable fibers are a blend of beet pulp, gum talha, and fructooligosaccharides. A preferred weight ratio of beet pulp to fructooligosaccharides in the fermentable fiber blend is from about 3:1 to 6:1, and most preferably 4:1. A preferred weight ratio of beet pulp to gum talha to fructooligosaccharide is 6:2:1.5. Beet pulp provides a source of butyrate to the intestinal cells of the animal.

Accordingly, it is a feature of the present invention to provide a pet food product and process for repartitioning nitrogen in dogs by increasing nitrogen excretion via the colon which provides a low cost, easy to administer method of reducing the amount of nitrogen in the blood of dogs without using the kidneys. It is a further feature of the present invention to provide a pet food product and method for increasing colonic blood flow in dogs to promote intestinal health. It is a further object of the present invention to provide a pet food composition containing fermentable fibers and method for enhancing metabolic fuel availability to canine intestinal cells. These, and other features and advantages of the present invention, will become apparent from the following detailed description, the accompanying drawings, and the appended claims.

DETAILED DESCRIPTION OF THE PREFERRED EMBODIMENTS

Figure 1:
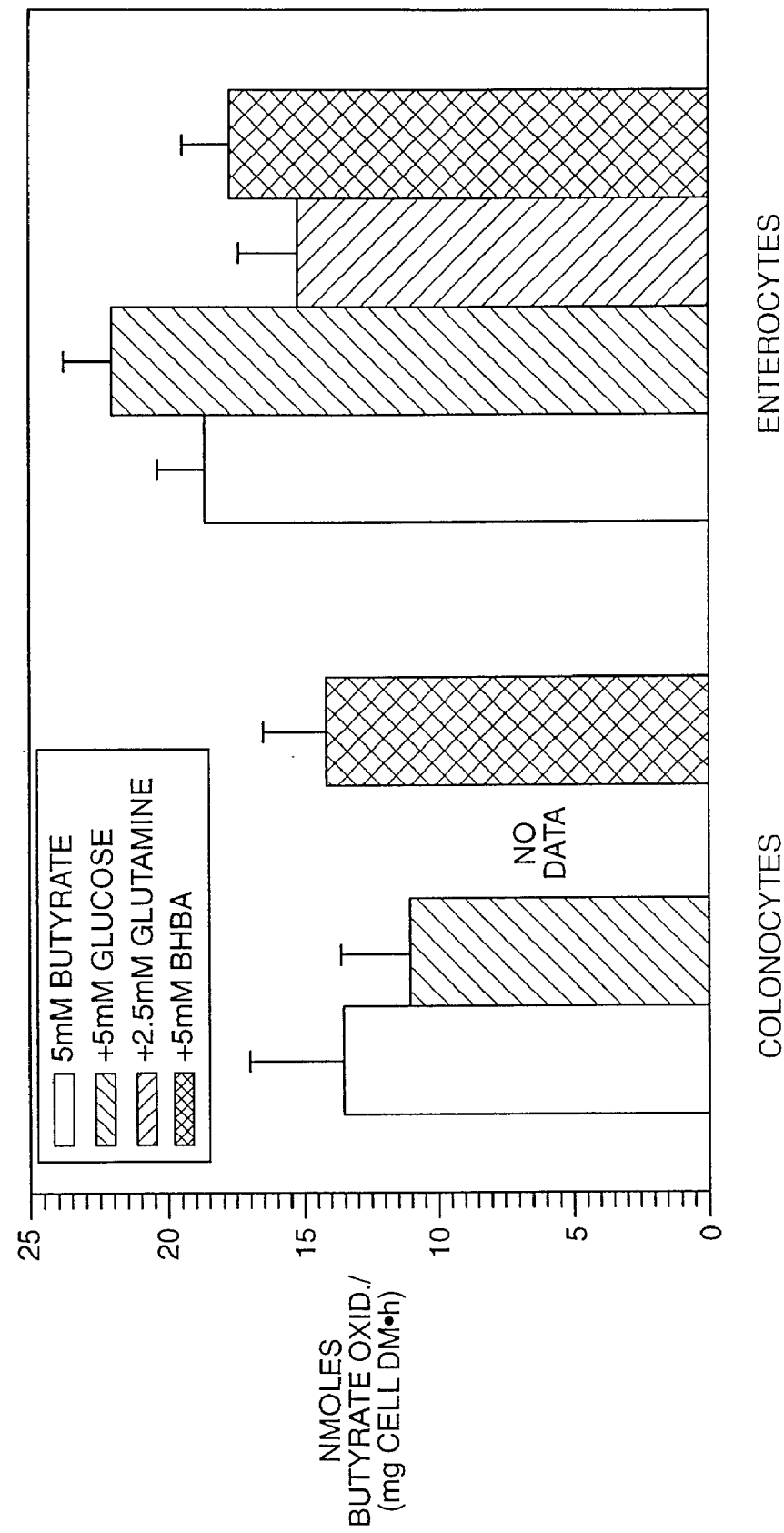
FIG. 1 shows the oxidation of [$1-^{14}C$] butyrate by the canine intestinal cells.

The present invention uses a pet food composition containing fermentable fibers to remove nitrogen from the blood of dogs, to enhance blood flow to colonic tissues, and to enhance metabolic fuel availability to canine intestinal cells. This is accomplished by adding fibers having a certain range of fermentability to a dog's diet. These fibers are a preferred nutritional source for bacteria in the colon, providing an increase in the quantity of bacteria in the colon. These bacteria also require nitrogen to reproduce. That nitrogen is derived from urea drawn into the intestinal lumen from the portal blood. Once it is inside the intestinal lumen, the nitrogen from urea and carbon skeletons from the fibers are synthesized into bacterial protein and consequently excreted in the feces.

The process of the present invention also increases colonic blood flow. Increased colonic blood flow promotes a healthy gut by keeping the colonic tissues infused with nutrients. While not wishing to be bound by any particular theory, the mechanism by which this blood flow increase occurs is believed to be either:

1) short chain fatty acids causing a relaxation of the resistance arteries of the colon; or,
2) short chain fatty acid absorption increasing intestinal metabolic activity, which elicits increased blood flow.

The process of the present invention also enhances metabolic fuel availability to canine intestinal cells. That is, the fermentation of the fibers in the small and large intestine of the animal produces short chain fatty acids such as, for example, butyrates which are utilized by canine enterocytes (cells in the small intestine) and colonocytes (cells in the large intestine). Thus, the process of the present invention provides both a direct fuel source to exogenous cell tissues in the small intestine and colon as well as an indirect fuel source (via increased colonic blood flow) to endogenous cell tissues.

Incorporation of fermentable fiber into the diet may also have several other beneficial effects. These include reducing colonic histopathologies, increasing the weight of colonic tissue or epithelial cell proliferation, and beneficially altering the intestinal microbiota. Short chain fatty acids (SCFAs) produced by fermentation of carbohydrates are associated with the trophic effects on colonic tissue and inhibition of potentially pathogenic intestinal microbiota.

The present invention uses a pet food composition containing fermentable fibers which display certain organic matter disappearance percentages. The fermentable fibers used in the present invention have an organic matter disappearance (OMD) of from about 15 to 60 percent when fermented by fecal bacteria in vitro for a 24 hour period. That is, from about 15 to 60 percent of the total organic matter originally present is fermented and converted by the fecal bacteria. The organic matter disappearance of the fibers is preferably 20 to 50 percent, and most preferably is 30 to 40 percent.

Thus, in vitro OMD percentage may be calculated as follows: {1-[(OM residue—OM blank)/OM initial]}×100, where OM residue is the organic matter recovered after 24 hours of fermentation, OM blank is the organic matter recovered in corresponding blank tubes (i.e., tubes containing medium and diluted feces, but no substrate), and OM initial is that organic matter placed into the tube prior to fermentation. Additional details of the procedure are found in Sunvold et al, J. Anim. Sci. 1995, vol. 73:1099–1109.

The pet food composition can be any suitable pet food formula which also provides adequate nutrition for the animal. For example, a typical canine diet for use in the present invention may contain about 30% crude protein, about 20% fat, and about 10% total dietary fiber. However, no specific ratios or percentages of these or other nutrients are required.

Fermentable fibers which are useful in the present invention produce short chain fatty acids (SCFAs) within a range of from about 28 to about 85 mmol SCFA per 1000 Calories (kcals) of metabolizable energy (ME), and more preferably within a range of from about 42 to about 71 mmol SCFA per 1000 ME kcals. This equates to a composition which has a total fermentable fiber content which yields from about 100 to about 350 mmol SCFA/kg of diet.

Millimoles of SCFAs per 1000 metabolizable energy kilocalories are calculated by first calculating the total Calories of metabolizable energy (ME) in a given diet composition per kilogram of the composition. The number of grams per 1000 kcal ME may be derived from the first calculation. Then the grams, and thus millimoles, of the fermentable fiber components of the composition may be calculated.

The fermentable fiber of the present invention may be any fiber source which intestinal bacteria present in the animal can ferment to produce significant quantities of SCFAs. "Significant quantities" of SCFAs, for purposes of this invention, are amounts over 0.5 mmol of total SCFAs/gram of substrate in a 24 hour period. Preferred fibers include beet pulp, gum arabic (including gum talha), psyllium, rice bran, carob bean gum, citrus pulp, pectin, fructooligosaccharides, mannanoligosaccharides and mixtures of these fibers.

The fermentable fibers are used in the pet food composition in amounts from 1 to 11 weight percent of supplemental total dietary fiber, preferably from 2 to 9 weight percent, more preferably from 3 to 7 weight percent, and most preferably from 4 to 7 weight percent.

A definition of "supplemental total dietary fiber" first requires an explanation of "total dietary fiber". "Total dietary fiber" is defined as the residue of plant food which is resistant to hydrolysis by animal digestive enzymes. The main components of total dietary fiber are cellulose, hemicellulose, pectin, lignin and gums (as opposed to "crude fiber", which only contains some forms of cellulose and lignin). "Supplemental total dietary fiber" is that dietary fiber which is added to a food product above and beyond any dietary fiber naturally present in other components of the food product. Also, a "fiber source" is considered such when it consists predominantly of fiber.

In order that the invention may be more readily understood, reference is made to the following examples which are intended to illustrate the invention, but not limit the scope thereof.

EXAMPLE 1

An experiment was conducted to determine the effect that dietary fiber fermentability had on bacterial excretion in the feces and the partitioning of waste nitrogen between the urine and the feces. Twenty purpose bred female Beagles were fed nutritionally complete diets that contained one of four fiber substrates: cellulose (low fermentability), beet pulp (moderate fermentability, moderate fermentation rate), fructooligosaccharide (FOS; moderately high fermentability, rapid fermentation rate) and a blend of gum talha, beet pulp, and FOS (see Table 1). The nitrogen content of the diet, urine, and lyophilized feces was determined and nitrogen balance calculated (See Tables 2–5). Bacterial nitrogen excretion was determined by analyzing lyophilized feces for purine concentration.

Feeding fermentable fiber to dogs decreased urinary nitrogen excretion and increased fecal nitrogen excretion. The increased fecal nitrogen occurred due to an increased microbial nitrogen excretion in the feces that resulted from fermentable fiber consumption. This experiment demonstrated that diet inclusion of fermentable fiber can partition waste nitrogen from the urine to the feces.

TABLE 1

Ingredient Composition of Basal Diet

| Ingredient | Percentage on a dry matter basis |
| --- | --- |
| Pre-gelatinized corn starch | to 100 |
| Poultry by-product meal | 43.5 |
| Poultry fat | 12.8 |
| Egg product | 2.4 |
| Chicken liver meal | 1.0 |
| Brewer's dried yeast | 1.0 |
| Monosodium phosphate | 1.0 |
| Calcium carbonate | 0.8 |
| Potassium chloride | 0.6 |
| Vitamins | 0.4 |
| Choline chloride | 0.3 |
| Minerals | 0.3 |
| DL-Methionine | 0.1 |
| Sodium chloride | 0.03 |
| Fiber source | * |

*Cellulose diet: Solka Floc 6.0%
Beet pulp diet: Beet pulp 6.0%
FOS diet: FOS 1.5%
Blend diet: Beet pulp 6.0%, Gum talha 2.0%, FOS 1.5%

TABLE 2

Dry Matter Intake and Digestibility of Diets Differing in Fiber Source

| | Cellulose | Beet Pulp | FOS | Blend |
| --- | --- | --- | --- | --- |
| Dry Matter Intake g/d | 258 | 224 | 195 | 225 |
| Dry Matter Digestibility % | 84 | 85 | 87 | 82 |

Intake was numerically lower and digestibility higher for the FOS diet.

TABLE 3

Nitrogen Excretion and Digestibility of Diets Differing in Source of Fiber

| | Cellulose | Beet Pulp | FOS | Blend |
| --- | --- | --- | --- | --- |
| Nitrogen intake g/d* | 13.1 | 12.8 | 10.1 | 12.1 |
| Fecal nitrogen output g/d | 1.6 | 1.8 | 1.2 | 2.0 |
| Urinary nitrogen output g/d | 7.7 | 6.0 | 4.2 | 6.7 |
| Nitrogen balance g/d | 3.8 | 5.0 | 4.7 | 3.4 |
| Nitrogen digestibility % | 87 | 86 | 86 | 83 |
| Fecal nitrogen % of nitrogen excreted | 17.2 | 23.1 | 22.2 | 23.0 |
| Urinary nitrogen % of nitrogen excreted | 82.8 | 76.9 | 77.8 | 77.0 |

*g/d = grams per day

Nitrogen intake tended to reflect the numerical differences observed in dry matter intake. Fecal nitrogen output was greatest for the Blend and Beet Pulp diets, intermediate for Cellulose and least for FOS diet. Urinary nitrogen output was numerically lower for dogs fed Beet Pulp, Blend, and FOS diets. Nitrogen balance was greater for Beet Pulp and FOS diets compared to Cellulose and Blend diets. Nitrogen digestibility was greatest for the Cellulose diet, intermediate for the FOS and Beet Pulp diets and lowest for the Blend diet. Fecal nitrogen expressed as a percentage of nitrogen excreted was greater for the Blend diet, FOS diet and Beet Pulp diets, as compared to the Cellulose diet. Urinary nitrogen output as a percentage of nitrogen intake was numerically greater with the Cellulose diet.

TABLE 4

Microbial Nitrogen, and Bicinchoninic Acid (BCA) True Protein in Feces of Dogs Fed Diets Differing in Source of Fiber

| | Cellulose | Beet Pulp | FOS | Blend |
| --- | --- | --- | --- | --- |
| Microbial nitrogen g/d | 0.37 | 0.51 | 0.38 | 0.54 |
| BCA true protein g/d | 0.95 | 1.26 | 0.67 | 1.48 |
| % BCA true protein | 9.5 | 11.2 | 8.9 | 11.8 |

Microbial nitrogen output was greatest for Blend and Beet Pulp diets and lowest for FOS and Cellulose diets. Output of bicinchoninic acid (BCA) true protein was greatest for Blend, intermediate for Beet Pulp and Cellulose diets, and least for the FOS diet. BCA true protein as a percentage of fecal DM was greater for Beet Pulp and Blend diets as compared to Cellulose and FOS diets.

TABLE 5

Blood Flow (ml/min/100 g of colon) through the colic artery of dogs

| | Time | | | | x (ml/min/100 g colon) |
| --- | --- | --- | --- | --- | --- |
| | 0600 | 1200 | 1630 | 2100 | |
| Cellulose | 12.3 | 14.8 | 10.7 | 12.0 | 12.5 |
| Beet Pulp | 13.9 | 14.1 | 12.7 | 12.2 | 13.2 |
| FOS | 22.6 | 15.0 | 11.7 | 12.4 | 15.4 |
| Blend | 17.6 | 14.8 | 13.9 | 13.4 | 14.9 |

The average blood flow to the colon was greatest with the FOS and Blend diets, intermediate with the Beet Pulp diet, and lowest with the Cellulose diet.

EXAMPLE 2

An in vitro experiment was conducted to determine the fermentability of fibrous substrates by dog fecal microflora. Feces from three female English Pointers were used as the inoculum source of anaerobic microflora. Substrates were fermented for 24 hours and then the concentrations of various short-chain fatty acids were determined. The results are shown in Table 7. The data shows that Solka Floc (a cellulose source) was essentially non-fermentable with an insignificant quantity of SCFAs being produced while lactulose was the most fermentable fiber. Fibers within the scope of the present invention, such as gum karaya, xanthan gum, gum arabic, beet pulp, gum talha, and carob bean produced moderate quantities of SCFAs, intermediate to that produced by the Solka Floc and lactulose. Also, beet pulp produced the highest quantity of butyrate, which is an important energy substrate for colonocytes.

TABLE 6

Short-Chain Fatty Acids produced by dog fecal bacteria on various fiber substrates in a 24 hour period

| Fiber Substrate | Short-Chain Fatty Acid (mmol/g organic matter) | | | |
| --- | --- | --- | --- | --- |
| | Acetate | Propionate | Butyrate | Total SCFA |
| Solka Floc | 0.09 | 0.05 | 0.00 | 0.14 |
| Oat Fiber | 0.19 | 0.14 | 0.03 | 0.35 |
| Gum Karaya | 0.61 | 0.01 | 0.02 | 0.64 |

TABLE 6-continued

Short-Chain Fatty Acids produced by dog fecal bacteria on various fiber substrates in a 24 hour period

| Fiber Substrate | Short-Chain Fatty Acid (mmol/g organic matter) | | | |
|---|---|---|---|---|
| | Acetate | Propionate | Butyrate | Total SCFA |
| Xanthan Gum | 0.80 | 0.10 | 0.05 | 0.95 |
| Gum Arabic | 0.62 | 0.47 | 0.40 | 1.49 |
| Beet Pulp | 2.03 | 0.80 | 0.70 | 3.01 |
| Gum Talha | 0.71 | 0.97 | 0.60 | 2.28 |
| Carob Bean | 2.10 | 1.44 | 0.65 | 4.19 |
| Locust Bean | 2.60 | 2.70 | 0.52 | 5.81 |
| FOS[1] | 2.86 | 2.52 | 0.30 | 5.67 |
| Pectin | 4.54 | 1.76 | 0.54 | 6.84 |
| Guar Gum | 3.07 | 3.79 | 0.41 | 7.26 |
| Lactulose | 3.47 | 4.52 | 0.35 | 8.34 |

[1]Fructooligosaccharides

EXAMPLE 3

In vitro experiments were conducted to determine the percentage of organic matter disappearance (OMD) of fibrous substrates when exposed to dog and cat fecal microflora. Three female English Pointers provided the fecal samples for the dog anaerobic microflora. Feces from one female and two male shorthairs were used as the inoculum source of the cat anaerobic microflora. The amount of organic matter was determined for various substrates. Then, these substrates were fermented for 24 hours and the amount of organic matter remaining was determined. The results, given as the percentage of OMD, are shown in Table 7. The data shows that Solka Floc (a cellulose source) had the smallest percentage of OMD while citrus pectin had the highest. Fibers within the scope of the present invention, such as beet pulp, citrus pulp, carob bean, and gum talha had intermediate OMD percentages.

TABLE 7

The Organic Matter Disappearance (%) of various substrates after being subjected to Dog and Cat Fecal Microflora for 24 hours

| Substrate | Dog Microflora | Cat Microflora |
|---|---|---|
| Solka Floc | 4.3 | 1.2 |
| Gum Karaya | 18.5 | 27.9 |
| Xanthan Gum | 28.0 | 21.1 |
| Gum Arabic | 24.6 | 28.5 |
| Beet Pulp | 38.2 | 35.0 |
| Gum Talha | 36.3 | 35.3 |
| Citrus Pulp | 44.3 | — |
| Carob Bean Gum | 49.8 | 47.8 |
| Locust Bean Gum | 61.7 | 72.2 |
| Guar Gum | 75.3 | 74.3 |
| Citrus Pectin | 84.9 | 83.8 |

EXAMPLE 4

An in vitro experiment was conducted to determine the fermentability of selected fiber sources by dog fecal microflora. Inocula came from dogs adapted to either a non-fermentable fiber-containing diet (Solka Floc, a cellulose source) or a fermentable fiber-containing diet (citrus pulp) within the scope of the present invention.

Feces from three English Pointers adapted to each diet were used as a source of microflora to evaluate short-chain fatty acid (SCFA) production from carob bean, citrus pulp, and citrus pectin substrates. The substrates were fermented for 6 and 12 hours. The results are shown in Tables 8 and 9.

The data indicates that acetate and total SCFA production was significantly greater after 6 and 12 hours of fermentation from dogs consuming the citrus pulp-containing diet, and may indicate that cellulose (Solka Floc) causes a depression in microbial activity.

TABLE 8

Acetate production (mmol/grain of organic matter) of Solka Floc and Citrus Pulp fibers on various substrates

| | Solka Floc fiber Incubation time (hours) | | Citrus Pulp fiber Incubation time (hours) | |
|---|---|---|---|---|
| | 6 | 12 | 6 | 12 |
| Carob bean substrate | 0.38 | 1.00 | 0.61 | 0.47 |
| Citrus pulp substrate | 0.59 | 1.39 | 1.28 | 2.00 |
| Pectin substrate | 0.54 | 1.54 | 1.15 | 3.02 |

TABLE 9

Total SCFA production (mmol/gram of organic matter) of Solka Floc and Citrus Pulp fibers on various substrates

| | Solka Floc fiber Incubation time (hours) | | Citrus Pulp fiber Incubation time (hours) | |
|---|---|---|---|---|
| | 6 | 12 | 6 | 12 |
| Citrus pulp substrate | 0.81 | 1.88 | 2.08 | 2.72 |
| Pectin substrate | 0.72 | 2.07 | 1.51 | 4.17 |

EXAMPLE 5

Enterocytes and colonocytes were isolated from the intestines of adult dogs and grown in vitro using procedures modified from Kight and Fleming, J. Nutr. Biochem. 6:27 (1995) and Marsman and McBurney, J. Nutr. 125:273 (1995). Metabolic fuel usage by the cells was determined by measuring production of $^{14}CO_2$ from radio-labelled substrates. Oxidation rates (nmoles substrate per hour per mg cell dry matter) for [$1\text{-}^{14}C$]-butyrate (5 mM), [$U\text{-}^{14}C$]-glucose (5 mM), and L-[$U\text{-}^{14}C$]-glutamine (2.5 mM) were 13.5±3.5, 6.5±96, and 8.1±21 for canine colonocytes and 18.7±1.7, 16.1±1.0, and 32.0±4.3 for canine enterocytes.

Figure 2:
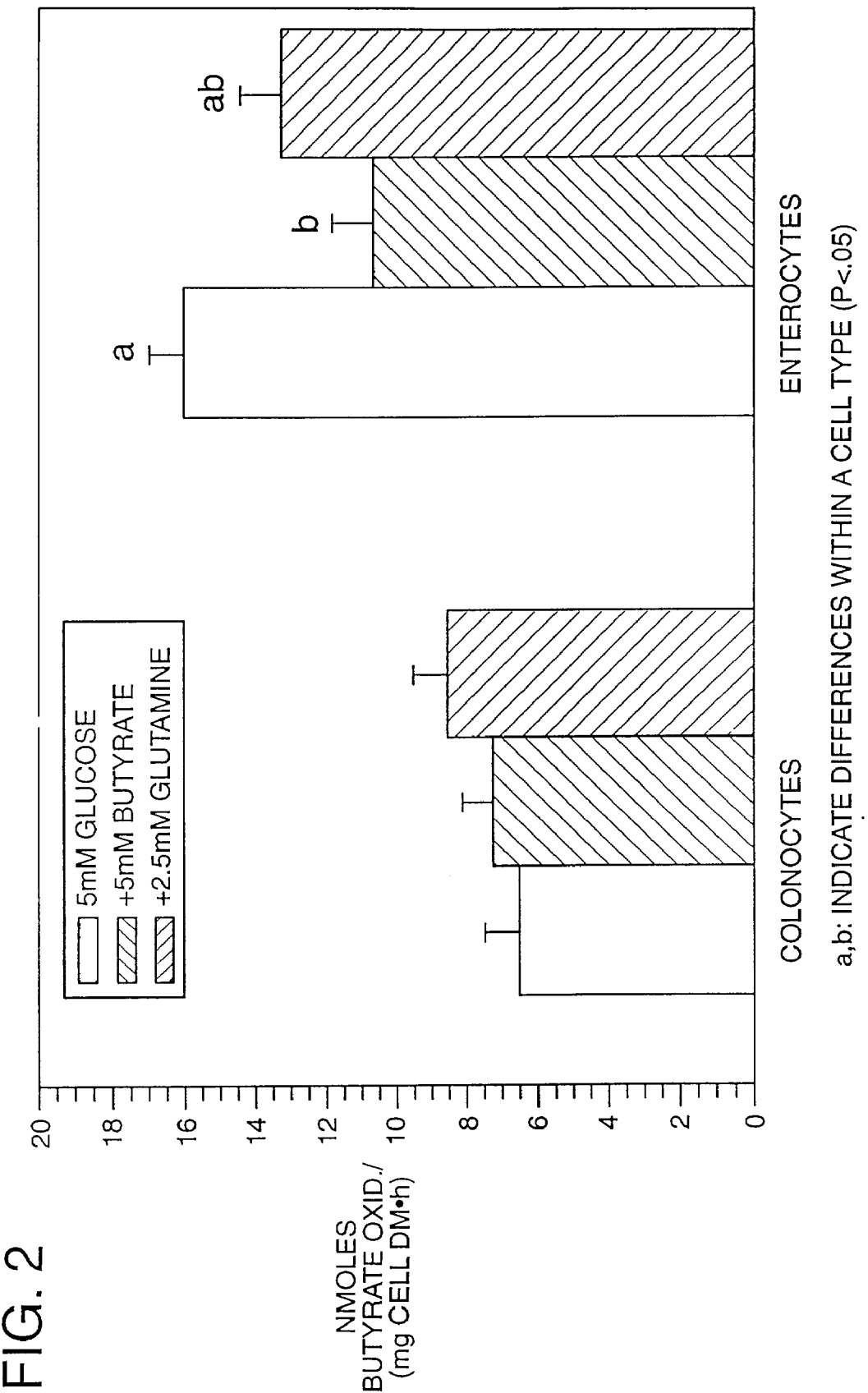
FIG. 2 shows the oxidation of [$U-^{4}C$] glucose by the canine intestinal cells.

FIG. 1 shows the oxidation of [$1\text{-}^{14}C$] butyrate by the canine intestinal cells. The oxidation of butyrate by colonocytes (cells in the large intestine) and enterocytes (cells in the small intestine) was not affected by medium supplementation with glucose (5 mM), glutamine (2.5 mM), or 9-hydroxybutyric acid (BHBA) (5 mM). FIG. 2 shows the oxidation of [$U\text{-}^{14}C$] glucose by the canine intestinal cells. The oxidation of glucose (5 mM) by colonocytes was not decreased by the addition of 2.5 mM glutamine or 5 mM β-hyroxybutyrate to the media. In contrast, the addition of butyrate decreased glucose oxidation by canine enterocytes.

From these results, canine enterocytes utilize butyrate with a greater affinity than glutamine or glucose, while canine colonocytes appear to utilize glucose and butyrate with equal affinity. The implications of these observed results indicate that feeding the dog a diet containing a source of fermentable fibers which break down into short chain fatty acids provides a source of metabolizable fuel to canine intestinal cells. Additionally, as canine intestinal cells utilize glucose as a source of fuel, the additional benefit of increased colonic blood flow resulting from a diet containing fermentable fibers enhances the availability of this important fuel source to intestinal cells.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for repartitioning nitrogen in dogs comprising:
feeding a dog a diet consisting essentially of a pet food composition containing fermentable fibers which have an organic matter disappearance of 15 to 60 percent when fermented by fecal bacteria for a 24 hour period, said fibers being present in amounts from about 1 to 11 weight percent of supplemental total dietary fiber, and
maintaining said dog on said diet for a sufficient period of time to allow said fermentable fibers to ferment in the colon of said dog, to increase the amount of nitrogen being excreted through the feces of said dog.

2. The process of claim 1 wherein said pet food composition contains from 2 to 9 weight percent of supplemental total dietary fiber of said fermentable fibers.

3. The process of claim 1 wherein said pet food composition contains from 3 to 7 weight percent of supplemental total dietary fiber of said fermentable fibers.

4. The process of claim 1 wherein said pet food composition contains from 4 to 7 weight percent of supplemental total dietary fiber of said fermentable fibers.

5. The process of claim 1 wherein said fermentable fibers have an organic matter disappearance of 20 to 50 percent.

6. The process of claim 5 wherein said fermentable fibers have an organic matter disappearance of 30 to 40 percent.

7. The process of claim 1 wherein said fermentable fibers are selected from the group consisting of beet pulp, gum arabic, gum talha, psyllium, rice bran, carob bean gum, citrus pulp, pectin, fructooligosaccharides, mannanoligosaccharides and mixtures thereof.

8. The process of claim 1 wherein said fermentable fibers are selected from the group consisting of beet pulp, gum arabic and fructooligosaccharides.

9. The process of claim 1 wherein said fermentable fibers are beet pulp.

10. The process of claim 1 wherein said fermentable fibers comprise a blend of beet pulp, gum talha and fructooligosaccharides.

11. A process for promoting colonic blood flow in dogs comprising:
feeding a dog a diet consisting essentially of a pet food composition containing fermentable fibers which have an organic matter disappearance of 15 to 60 percent when fermented by fecal bacteria for a 24 hour period, said fibers being present in amounts from about 1 to 11 weight percent of supplemental total dietary fiber, and
maintaining said dog on said diet for a sufficient period of time to increase colonic blood flow in said dog.

12. A process for providing short chain fatty acids to the large and small intestines of a dog to improve metabolic fuel availability to canine intestinal cells comprising the steps of:
feeding a dog a diet consisting essentially of a pet food composition containing fermentable fibers which have an organic matter disappearance of 15 to 60 percent when fermented by fecal bacteria for a 24 hour period, said fibers being present in amounts from about 1 to 11 weight percent of supplemental total dietary fiber, and
maintaining said dog on said diet for a sufficient period of time to allow said fermentable fibers to ferment in the colon of said dog and provide said short chain fatty acids.

13. The process of claim 12 wherein said fermentable fibers include beet pulp which ferments to produce butyrate.

14. A pet food product comprising a composition containing fermentable fibers, said fermentable fibers comprising a blend of beet pulp, gum talha or gum arabic and fructooligosaccharides, which fermentable fibers have an organic matter disappearance of 15 to 60 percent when fermented by fecal bacteria for a 24 hour period, said fibers being present in amounts from about 1 to 11 weight percent of supplemental total dietary fiber.

15. The pet food product of claim 14 wherein the weight ratio of beet pulp to fructooligosaccharides is from about 3:1 to 6:1.

16. The pet food product of claim 14 wherein the weight ratio of beet pulp to gum to fructooligosaccharides is 6:2:1.5

17. The pet food product of claim 14 in which the total fermentable fiber content of said composition yields from about 100 to about 350 mmol SCFA/kg of diet.

18. The pet food product of claim 14 in which said composition comprises about 30% crude protein, about 20% fat, and about 10% total dietary fiber.

19. The pet food product of claim 14 wherein said pet food composition contains from 2 to 9 weight percent of supplemental total dietary fiber of said fermentable fibers.

20. The pet food product of claim 14 wherein said pet food composition contains from 3 to 7 weight percent of supplemental total dietary fiber of said fermentable fibers.

21. The pet food product of claim 14 wherein said pet food composition contains from 4,to 7 weight percent of supplemental total dietary fiber of said fermentable fibers.

22. The pet food product of claim 14 wherein said fermentable fibers have an organic matter disappearance of 20 to 50 percent.

23. The pet food product of claim 14 wherein said fermentable fibers have an organic matter disappearance of 30 to 40 percent.

* * * * *